United States Patent [19]

Doussiet

[11] Patent Number: 4,671,100

[45] Date of Patent: Jun. 9, 1987

[54] PERMEAMETER

[75] Inventor: Roger Doussiet, Lezat sur Leze, France

[73] Assignee: Societe Nationale Elf Aquitaine (Production), Courbevoie, France

[21] Appl. No.: 851,738

[22] Filed: Apr. 14, 1986

[30] Foreign Application Priority Data

Apr. 15, 1985 [FR] France ................. 85 05601

[51] Int. Cl.$^4$ ............................................. G01N 15/08
[52] U.S. Cl. ............................................ 73/38
[58] Field of Search ........................................... 73/38

[56] References Cited

U.S. PATENT DOCUMENTS

| | | | |
|---|---|---|---|
| 2,705,418 | 4/1955 | Reichertz et al. | 73/38 |
| 2,713,789 | 7/1955 | Kelton | 73/38 |
| 3,139,747 | 7/1964 | Ferrell et al. | 73/38 |
| 3,140,599 | 7/1964 | Rahme | 73/38 |
| 3,405,553 | 10/1968 | Boisard et al. | 73/38 |
| 3,636,751 | 1/1972 | Pasini | 73/38 |
| 4,385,517 | 5/1983 | Sorce | 73/38 |
| 4,555,934 | 12/1985 | Freeman et al. | 73/38 |
| 4,573,342 | 3/1986 | Jones | 73/38 |

Primary Examiner—Stewart J. Levy
Assistant Examiner—Joseph W. Roskos
Attorney, Agent, or Firm—Holman & Stern

[57] ABSTRACT

A process and apparatus for measuring the permeability of solid samples involves applying a constant differential pressure between the end faces of a sample disposed in a measuring cell, introducing a pressurized gas into the sample for a specified time, measuring the fluid flow rate, and then calculating the permeability of the sample by applying Darcy's law.

12 Claims, 3 Drawing Figures

PERMEAMETER

BACKGROUND AND SUMMARY OF THE INVENTION

The present invention relates to a device and to a process for the automatic measurement and recording of the permeability of solid samples, such as cores of mineral materials obtained from drill-holes in the ground.

Knowledge of the permeability of a rock is an important parameter for assessing the capacity of a fluid, namely a gas or a liquid, to circulate in the pores of the component material of the rock.

For many years, the permeability of rocks was measured manually by means of conventional permeameters, entailing the constant presence of an operator to monitor a pressure difference to be applied between the end faces of the generally cylindrical sample and to measure the flow time of a certain volume of fluid through the said sample, the fluid usually being a gas.

Measuring the transit time of a known volume of gas through the sample makes it possible, by applying Darcy's Law, to determine the permeability of the sample being studied.

To overcome the disadvantage of carrying out the abovementioned measurements manually, a process and a device, such as are described in French Pat. No. 1,388,740, have been proposed. The process involves transferring in sequence each of the samples to be studied from a pile arranged in a feed chute towards a measuring cell comprising a diaphragm capable of being deformed so as to seal off the lateral face of the sample introduced into the said cell, isolating one of the end faces of the sample from the ambient atmosphere, passing a gas stream at a given pressure through the sample from the isolated face, and then measuring the transit time of a predetermined volume of gas through the sample.

The process briefly described above and the device for carrying it out have two serious disadvantages.

The first is that each sample to be studied falls into the master cylinder as a result of gravity, before being pushed into the measuring cell, and such a fall can cause damage to the said sample and generate dust which has to be eliminated and prevented from being introduced into the measuring cell, failing which the sample could not be sealed off laterally in an effective way and the measurement would be subject to error.

The second disadvantage is much more important if the measurement is to be made fully automatic. In fact, the type of material varies from one sample to another, and consequently the permeability values to be measured vary within a range between 0 and 6 Darcys. Under these conditions, if a suitable permeability value is not obtained for a given pressure difference and a given gas volume, the pressure difference to be applied between the faces of the sample and the volume of gas introduced have to be readjusted by hand.

It will be appreciated that such a device is not suitable for appropriate automation of the permeability measurements.

The main subject of the present invention is an automatic device for measuring the permeability of a large number of samples in a relatively short time.

The process according to the invention is characterized in that it involves applying a constant differential pressure between the end faces of the sample which are arranged in a measuring cell, introducing a pressurized gas into the said sample for a constant time, measuring the fluid flowrate, and then calculating the permeability of the said sample by applying Darcy's Law.

One advantage of the present invention is that the pressure difference applied to the two faces of the sample is adjusted automatically as a function of the measured fluid flowrate, so as to obtain as accurate a permeability value as possible.

Another advantage is that the samples are introduced into the measuring cell automatically and in sequence, the sample being guided constantly during its movement. Other advantages and characteristics will emerge more clearly from a reading of the description of a preferred embodiment given as an illustrative, but non-limiting example, and from the attached drawing in which:

DESCRIPTION OF THE PREFERRED EMBODIMENT

Figure 1:
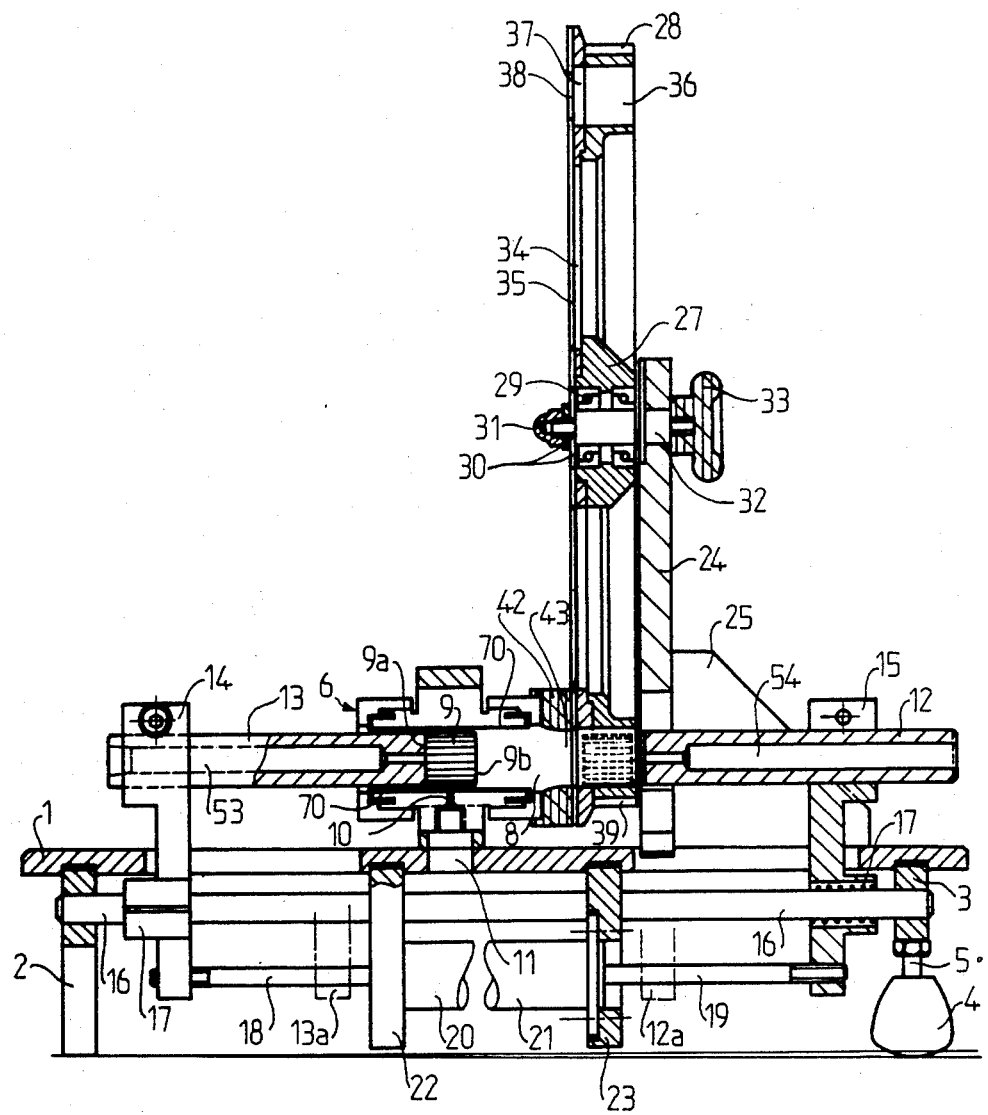
FIG. 1 is a sectional view of the device according to I—I of FIG. 2.

The device according to the invention, illustrated in the FIGS., comprises a base 1 resting on feet, of which a front foot 2 and a rear foot 3 are shown in FIG. 1. The horizontal position of the base 1 is ensured by means of a control handle 4 for a positioning rod 5.

A measuring cell 6 is mounted horizontally in a bearing 7 which is integral with the base 1. The cell 6 is of the type sold by Messrs. Hassler and comprises a flexible diaphragm 10 delimiting a measuring chamber 8, into which is introduced a sample 9, the permeability of which is to be measured. A duct 10 is formed in the cell 6 and connects the rear face of the diaphragm 70 to a pneumatic pressurizing source (not shown) via a passage 11 made in the base 1.

Two hollow pushers 12 and 13 for feeding and ejecting samples 9 are capable of moving partially in the measuring chamber 8. Each hollow pusher 12, 13 is integral with a support 14, 15 capable of sliding along a guide rod 16 which is arranged underneath the base 1 and which is mounted between the feet of the base. Each support 14, 15 has a ball cage 17 making sliding easier, this being effected by means of rods 18, 19 or control jacks 20, 21 which are mounted on vertical supports 22, 23.

Figure 2:
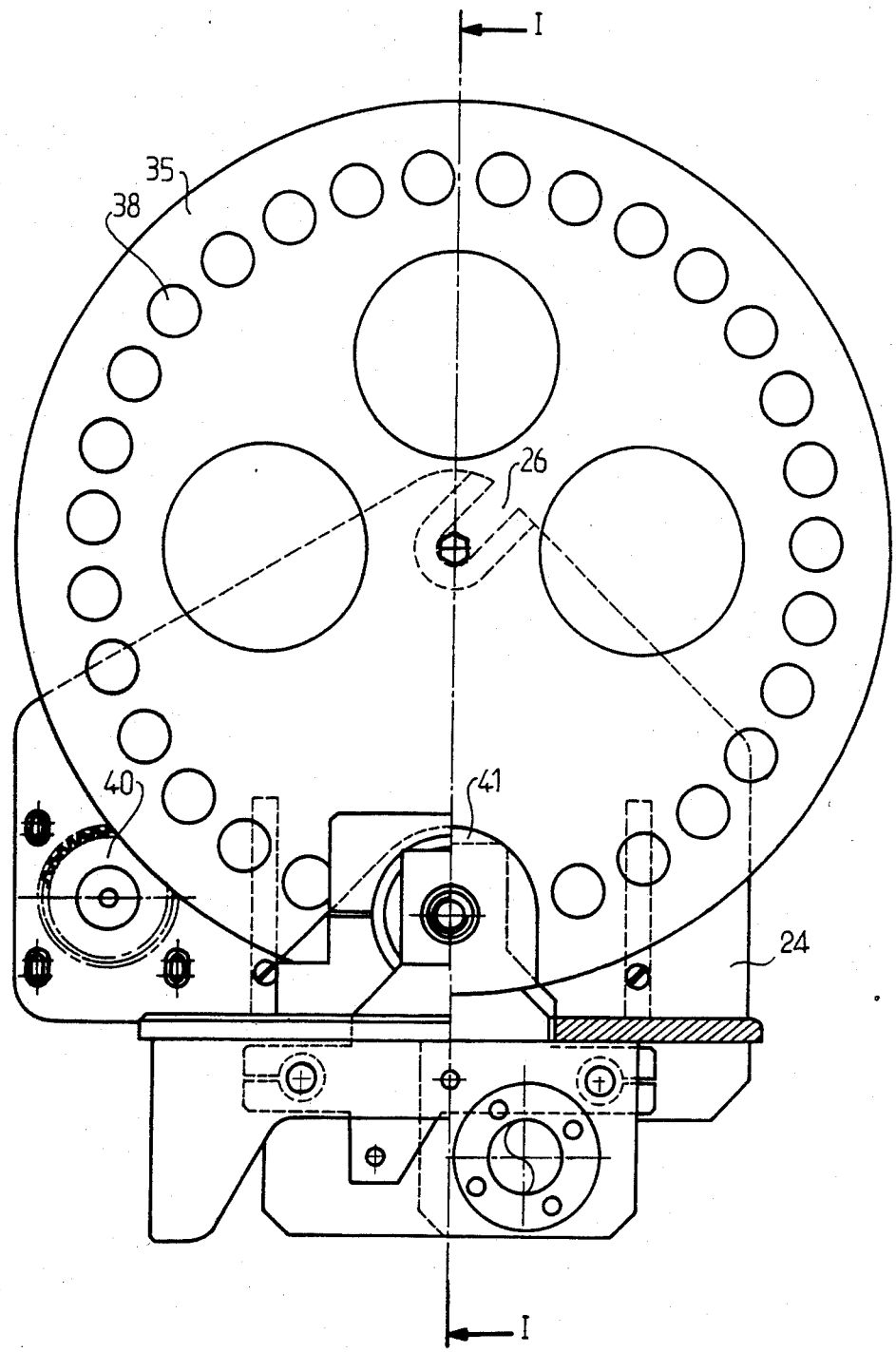
FIG. 2 is an elevation view of the device according to the invention.

A vertical support 24 is mounted fixedly on the base 1, and the vertical position can be ensured, in particular, by means of one or more stiffening brackets 25, and the vertical support 24 receives in a fork 26 (FIG. 2) a hub 27 of a turret 28. The hub 27 has rolling bearings 29, and the assembly for fastening the said hub comprises the usual elements, namely washers 30 and a blind nut 31. A clamping bolt 33 makes it possible to immobilize the turret 28 on the vertical support 24. A protective blank 34 and a transparent stop disk 35 are mounted in front of the turret 28 and on the axle 32 of the hub 27. Receptacles 36 for the samples 9 are formed in the turret 28 and are distributed uniformly over the entire periphery. The dimensions of the receptacles 36 are such that they can receive different types of samples 9, the length of which is usually between 20 and 28 mm. The protective blank 34 has orifices 37, the diameter of which is equal to that of the receptacles 36, whilst the stop disk 35 likewise has opposing orifices 38 of smaller diameter, the axes of the orifices 37, 38 and of the receptacles 36 being aligned with one another. The stop disk 35 forms an abutment for the samples 9 during the rotation of the turret 28, whilst the orifices 38 are used for the possible manual extraction of a sample 9 from its receptacle 36.

The turret 28 has a toothed ring 39 engaging with a pinion 40 (FIG. 2) controlled in terms of rotation by a stepping motor. The stop disk 35 has a notch 41 (FIG. 2), making it possible to transfer a sample 9 from its receptacle 36 through the opposing orifice 37 of the protective blank 34 towards the measuring chamber 8.

A sample guide 42 is located between the protective blank 34 and the measuring cell 8. A passage 43 in the form of a converging and diverging nozzle is made in the guide 42, making it possible to guide and align the sample to be measured in the said measuring chamber.

The device according to the invention operates as follows:

A sample 9 is placed in each receptacle 36 of the turret 28 which, for example, has thirty of these. The turret 28 is mounted in the fork 26 of the vertical support and clamped by means of the control knob 33. Consequently, the turret 28 can rotate, without being able to move laterally. It should be noted that the protective blank 34 which is integral with the turret likewise rotates, but that the stop disk remains fixed without the possibility of rotating. By means of a stepping motor (not shown), the turret 28 is positioned in such a way that a sample 9, represented by broken lines on the right of FIG. 1, is opposite the guide 42.

Figure 3:
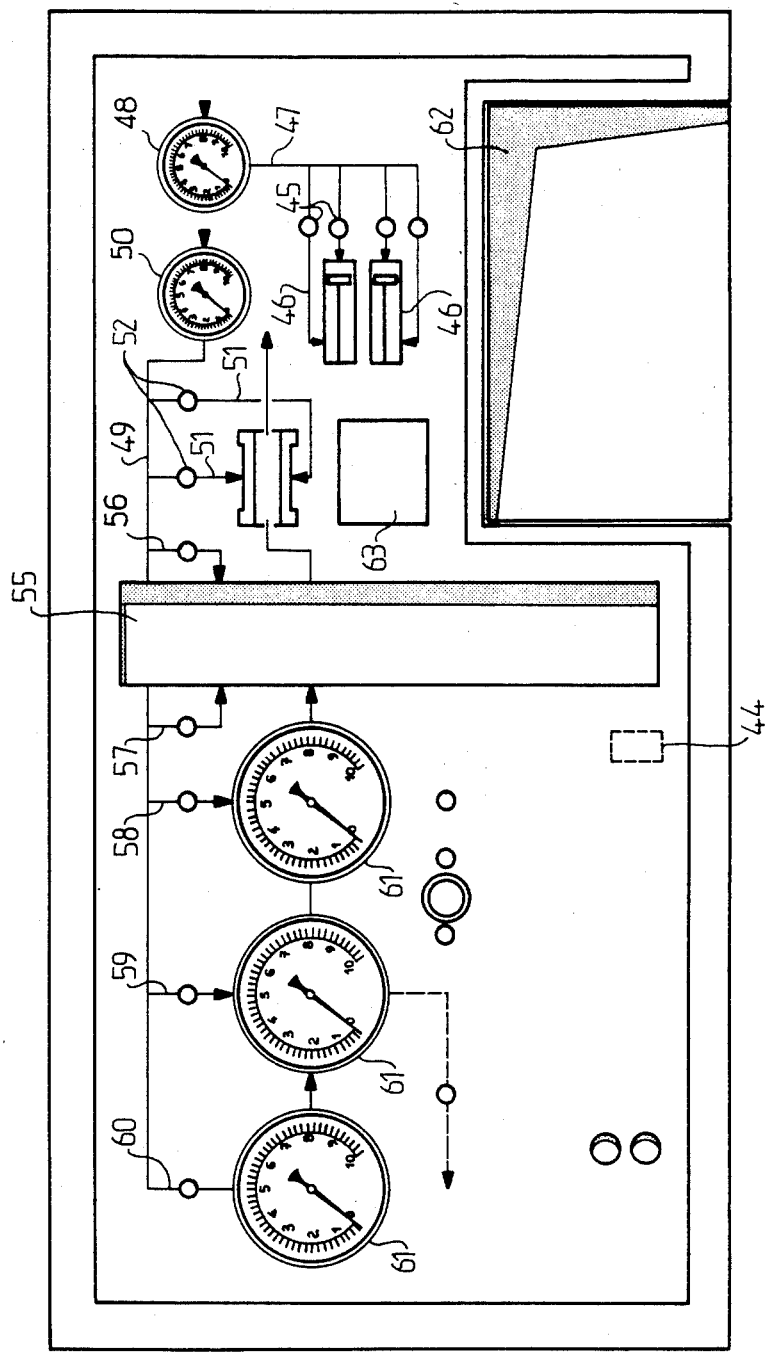
FIG. 3 is a diagrammatic view of the control desk of the device.

The various members controlling the jacks are not shown in detail, but are well known to a person skilled in the art, and they can consist, for example, of solenoid servo-valves. In FIG. 3, the solenoid valves as a whole are represented by a block 44 indicated by broken lines, whilst the jacks 20 and 21 are shown diagrammatically, with electroluminescent diodes 45 mounted on secondary feed-pipes 46 connected to a main feed-pipe 47, on which a pressure gauge 48 is mounted.

The pusher 13 is brought into the forward position, its front end being introduced into the measuring chamber 9, as shown in FIG. 1, the rear or retracted position being represented by broken lines and designated 13a. The stroke of the pusher 13 is, for example, 70 mm. When the pusher 13 is in the forward position, the pusher 12 is subsequently moved by controlling the jack 21, so as to extract the sample 9, represented by broken lines in FIG. 1, from its receptacle 36 in the turret 28 and introduce it into the chamber 8, until the face 9a of the sample comes up against the head of the pusher 13. The stroke of the pusher 12, the retracted position of which is represented by broken lines and designated 12a, is, for example, 75 mm. Since the position of the pusher 13 in the chamber 8 is fixed at each measurement, there is consequently an easy means of determining the length of the sample 9, this dimension being involved in calculating the permeability. In fact, by means of a linear potentiometer integral with the pusher 12, the said length of the sample 9 is determined. When the latter is arranged correctly in the chamber 8, in particular by being guided in the guide 42, the jack 12 is brought towards the retracted position 12a.

Pressurized fluid is then introduced into the duct 10, in order to deform the diaphragm 70 and lay it against the lateral wall of the sample 9, ensuring that the said sample is sealed off at the said lateral wall and immobilized during the entire phase of permeability measurement. The diaphragm 70 subjected to a pressure taken from a general feed-pipe 49 connected to a pressure source (not shown) via a pressure gauge 50, and by means of two small pipes 51, each equipped with an electroluminescent diode 52.

Of course, the length of the sample 9 can be determined by recording the movement stroke of the jack 13.

A gas coming from a source (not shown) feeds a channel 53 made in the pusher 13, so as to diffuse in the sample by entering via the face 9a and leaving via the face 9b which communicates with the ambient medium by means of the passage 43 and a channel 54 formed in the pusher 12.

The flow of gas through the sample 9 is measured by means of a mass flowmeter which utilizes the heat exchange by means of the gas via a capillary tube heated by two windings, the resistance of which varies with the temperature. Such a flowmeter is arranged on the base 1 at the rear of the jack 13 in FIG. 1 and is sold by Messrs. MKS under the reference 258. The gas flow-rates through the flowmeter in question are between 0 and 200 cm$^5$/minute, the accuracy being of the order of ±0.5%.

Since the permeabilities to be measured vary between 0 and 6 Darcys, the present invention proposes to exert on the face 9a of the sample 9 pressures varying from 10 g to 7 bars, in order to cover the entire range of potential permeabilities. The different pressures exerted in sequence and in the order described below are taken from the general pipe 49 by means of secondary pipes 56 to 60 corresponding respectively to 10 g, 65 g, 500 g, 2.5 bars and 7 bars, the pipes 58 to 60 each being equipped with a pressure gauge 61. The pressure of 2.5 bars is used for calibrating the flows.

A pressure of 10 g is first exerted on the face 9a of the sample 9 introduced into the measuring cell 8, and then the flow Q is measured after a waiting time of 30 seconds.

When $Q > 200$ cm$^3$/minute, a permeability of $K > 6,000$ md is displayed on a screen of a computer 62.

At $50 < Q < 200$ cm$^3$/minute, the device measures the flow Q and calculates the corresponding permeability K.

At $Q < 50$ cm$^3$/minute, an automatic control effected by switching means of a computer 62 applies the pressure of 65 g to the face 9a of the sample 9. If the flow Q is between 20 and 200 cm$^3$/minute, it is measured and the corresponding permeability K is calculated.

At $Q < 20$ cm$^3$/minute, the applied pressure changes to 2.5 bars. For a measurable and significant flow Q, the permeability K is calculated, otherwise the pressure of 7 bars is applied.

When the flow is zero, the computer does not calculate the permeability and indicates that K is less than 0.01 md.

When the measurement is completed, the pusher 13 is controlled to move towards its most advanced position, the effect of which is to extract the sample 9 from the chamber 8 and return it to its receptacle 36 in the turret 28.

The stepping motor subsequently controls the rotation of the turret 28 which brings another sample 9 opposite the guide 42, in order to introduce it into the measuring cell 6.

A recorder 63 of the mini-cassette type is used to record all the measurements made by the computer 62 and, if appropriate, the parameters necessary for studying the samples. The recorder 63 used makes it possible to store the data relating to approximately 1,900 samples.

Obviously, the electronic part will not be described in detail, nor will ancillary functions, such as malfunctions, irregular samples, sound and/or visual alarms.

Of these ancillary functions, it may be mentioned, as a reminder, that the flowmeter is calibrated by means of a calibrating valve connected to the pressure gauge 61 at 2.5 bars, whilst the potentiometric sensor for determining the length of the sample 9 to be studied is calibrated by introducing a standard sample into the measuring cell 6. The zero and the gain are set by means of two potentiometers, the values of which are validated and recorded when the setting is considered correct; such a setting is useful for samples of a length between 20 and 28 mm; whenever a sample of a length not contained between these limits is introduced, an alarm is triggered and the said sample is removed from the measuring cell 6 and returned to its receptacle 36.

Of course, the invention is in no way limited to the exemplary embodiment described and illustrated and can have many alternative forms accessible to a person skilled in the art, depending on the intended uses and without thereby departing from the scope of the invention.

I claim:

1. Device for the automatic measurement of the permeability of solid samples, of the type comprising means for receiving samples, a measuring cell having a horizontal axis, means for introducing each sample into and extracting it from the measuring cell, means for applying a pressurized fluid to one face of the sample, means for measuring the fluid flow passing through the sample arranged in the cell, and means for calculating the permeability of the sample, characterized in that the receiving means comprises a vertical turret which has, distributed uniformly over its entire periphery, receptacles for receiving the said samples and an axis of rotation substantially parallel to the axis of the measuring cell, characterized in that a protective blank is integral with the turret and is mounted between the said turret and a guide, which is interposed between the measuring cell and the turret, the said protective blank having orifices of the same dimensions as and opposite the receptacles of the turret.

2. Device according to claim 1, characterized in that the guide has a converging and diverging passage for guiding the sample between the turret and the measuring cell.

3. Device according to claim 1, characterized in that a stop member fixed in terms of rotation is mounted between the turret and the measuring cell, the said stop member having further orifices of smaller diameter than the orifices in the blank, but aligned with the latter, and in that a notch is made in the region of the guide, to allow the sample to pass from the turret towards the said guide.

4. Device according to claim 3, characterized in that the stop member is transparent.

5. Device according to claim 1, characterized in that the turret has an engaging ring interacting with a pinion driven by a stepping motor.

6. Device according to claim 1, characterized in that the means of introducing each sample into and extracting it from the measuring cell comprises hollow pushers, each being integral with a support capable of sliding along a fixed guide rod, the movement of each support being effected by means of a jack.

7. Device according to claim 1, characterized in that the measuring cell is integral with a base, the horizontal position of which is adjusted by means of a control handle.

8. Process for automatically measuring the permeability of a solid sample, characterized in that it involves applying a constant differential pressure between the end faces of the sample which are arranged in a measuring cell, introducing a pressurized gas into the said sample for a constant time, measuring the fluid flowrate, and then calculating the permeability of the said sample by applying Darcy's law, characterized in that successive differential pressures are applied in sequence as a function of the flowrates measured.

9. Process according to claim 8, characterized in that the length of each sample is measured automatically after it has been introduced into the measuring cell.

10. Process according to claim 8, characterized in that the transit time of the pressurized fluid is approximately 30 seconds.

11. Process according to claim 8, characterized in that the differential pressures are between 10 g and 7 bars.

12. Process according to claim 8, characterized in that all the parameters relating to each sample are recorded on a magnetic tape.

* * * * *